(12) United States Patent
Orr

(10) Patent No.: US 6,440,177 B1
(45) Date of Patent: Aug. 27, 2002

(54) ONE-STEP BLEACH AND COLORING COMPOSITION FOR HAIR AND METHOD OF USING SAME

(75) Inventor: Cindy L. Orr, Port Washington, NY (US)

(73) Assignee: Artec Systems Group, Port Washington, NY (US)

( * ) Notice: Subject to any disclaimer, the term of this patent is extended or adjusted under 35 U.S.C. 154(b) by 18 days.

(21) Appl. No.: 09/765,243

(22) Filed: Jan. 18, 2001

Related U.S. Application Data

(60) Provisional application No. 60/176,778, filed on Jan. 19, 2000.

(51) Int. Cl.$^7$ ................................................. A61K 7/13
(52) U.S. Cl. ................... 8/426; 8/654; 8/657; 8/659; 8/102; 8/110; 8/111; 424/62; 132/208; 132/209
(58) Field of Search ................ 8/426, 431, 654–657, 8/102, 110, 111; 424/62; 132/208, 209

(56) References Cited

U.S. PATENT DOCUMENTS

| | | | | |
|---|---|---|---|---|
| 2,991,228 | A | 7/1961 | Lusting | 167/88 |
| 3,193,464 | A | 7/1965 | Edman et al. | 167/88 |
| 3,578,387 | A | 5/1971 | Zviak et al. | 8/10.1 |
| 3,679,347 | A | 7/1972 | Brown | 8/10.1 |
| 3,912,446 | A | 10/1975 | Zviak et al. | 8/10.1 |
| 3,930,792 | A | 1/1976 | Alperin et al. | 8/10.1 |
| 4,027,008 | A | 5/1977 | Sokol | 424/62 |
| 4,138,478 | A | 2/1979 | Reese et al. | 424/62 |
| 4,226,852 | A | 10/1980 | Tesmann et al. | 424/62 |
| 4,247,537 | A | 1/1981 | Lunn et al. | 424/62 |
| 4,507,278 | A | 3/1985 | DeMarco et al. | 424/62 |
| 4,532,127 | A | 7/1985 | Feinland et al. | 424/62 |
| 4,886,517 | A | 12/1989 | Buguat et al. | 8/416 |
| 5,102,655 | A | 4/1992 | Yoshihara et al. | 424/62 |
| 5,196,029 | A | 3/1993 | Kawase et al. | 8/405 |
| 5,224,964 | A | 7/1993 | Shami | 8/405 |
| 5,226,924 | A | 7/1993 | Junino et al. | 8/405 |
| 5,279,313 | A | 1/1994 | Clausen et al. | 132/208 |
| 5,294,436 | A | 3/1994 | Cope et al. | 424/62 |
| 5,575,989 | A | 11/1996 | Caskey | 424/62 |
| 5,637,115 | A | 6/1997 | Blazer et al. | 8/407 |
| 5,660,190 | A | 8/1997 | Tricaud et al. | 132/208 |
| 5,688,291 | A | 11/1997 | Said et al. | 8/431 |
| 5,866,107 | A | 2/1999 | Schultz et al. | 424/62 |
| 5,879,412 | A | 3/1999 | Rondeau et al. | 8/411 |
| 5,888,484 | A | 3/1999 | Schmitt et al. | 424/62 |
| 5,891,200 | A | 4/1999 | Lim et al. | 8/426 |
| 6,007,585 | A | 12/1999 | Syed et al. | 8/432 |
| 6,045,591 | A | * | 4/2000 | Deneulenaere | |

\* cited by examiner

*Primary Examiner*—Margaret Einsmann
(74) *Attorney, Agent, or Firm*—Kramer, Levin, Naftalis & Frankel LLP

(57) ABSTRACT

In the present invention there is provided a single-step process and composition of hair bleach, which can simultaneously lighten the hair up to seven levels and effectively neutralize any undesirable warmth, provide natural tones or deposit fashion shades. This is achieved by including in the bleach mixture a solution containing basic dye molecules, which in the present invention have been found to be both, stable in the bleach, and capable of depositing the desired amount of tone on the hair. The dyes fall into the class of water-soluble basic azo compounds.

20 Claims, No Drawings

ONE-STEP BLEACH AND COLORING COMPOSITION FOR HAIR AND METHOD OF USING SAME

CROSS-REFERENCE TO RELATED APPLICATIONS

The present application claims the benefit of priority from U.S. application serial No. 60/176,778, filed Jan. 19, 2000.

FIELD OF THE INVENTION

The present invention relates generally to hair bleach and coloring compositions capable, in a single step, of lightening hair color by as much as seven levels while simultaneously depositing color tones that may either neutralize the warmth generated by the bleaching treatment, or add other desirable colors to the lightened hair; and methods of using such one-step bleach and coloring compositions.

BACKGROUND OF THE INVENTION

Inside the cortex of the hair fiber is the substance called melanin. Melanin is what gives the hair its natural color. It is the pigment of the hair. Two general classes of such pigments have been identified: eumelanins (characteristically brownish black) and pheomelanins (characteristically reddish orange). The concentration and combination of these two types of pigments are responsible for the natural color of hair. Dark hair has a higher concentration of the eumelanin, while red hair contains more pheomelanin. Light hair has reduced levels of both.

Hair bleaching is a chemical process by which a bleaching agent gradually destroys the melanin granules in the cortex, resulting in a lighter color of the hair. When an ammonical solution of hydrogen peroxide diffuses through the cuticle and enters the cortex, it starts to attack and disperse the melanin granules. The different types of melanin granules are not destroyed at the same rate. Generally, the eumelanins are easier to breakdown than the pheomelanins. Because of this property, dark hair, when bleached, experiences a visual enhancement of the red pigments during the bleaching process, and the casting of a reddish orange or "brassy" tone to the resultant bleached hair. In order to neutralize this warmth, hair colorants of a generally drabbing nature are typically applied during or after a bleaching treatment.

U.S. Pat. No. 5,688,291 to Said classifies hair bleach into two categories based on chemical composition and strength. "Category 1" bleaches are mild liquid or crème compositions typically utilizing alkaline hydrogen peroxide solutions and the like to oxidize and bleach the melanin. These compositions are generally used in conjunction with a hair coloring process. These compositions may lighten the hair as much as four levels at the most. Where category 1 bleaches are being used with commercial permanent hair colorants, the toners are mostly in the form of oxidative dyes. Some may contain Direct, Disperse, Acid or Basic dyes or combinations thereof. The environment of this type bleach is mild enough to allow the survival of several types of dyes. Typically, these category 1 bleach and coloring compositions will neutralize brassiness and produce natural and fashion shades but are limited in the amount of lightening.

"Category 2" bleaches are generally stronger than category 1 bleaches and are capable of over seven levels of lift, or lightening. They are utilized whenever more than four levels of lift are desired, such as when lifting light brown hair or darker to a pale blonde.

Category 2 bleaches are typically powder compositions based on persulfate salts of ammonium, potassium or sodium as booster supplies of active oxygen and silicate and/or carbonate salts as sources of alkalinity. Just before use, the powders are mixed with hydrogen peroxide solutions to form a workable crème that can be applied to hair. The working crème preferably has an alkaline pH to increase the speed of the oxidation reaction of the melanin for lightening and to swell the hair fiber to facilitate penetration of the product. For example, the pH of these systems is generally from about 9 to about 11. Some powder bleaches have hydrogen peroxide incorporated in a solid form, such as urea peroxide or sodium percarbonate and potassium percarbonate (see e.g., U.S. Pat. No. 5,575,989) to be mixed with water to activate. Quite often, a third separately packaged component, typically referred to as bleach oil, which may contain humectants and other conditioning agents and the like, is added to the bleach powder and peroxide at the time of use.

Because of the underlying tones that are exposed at the various levels of bleaching, a toning or coloring process to neutralize the warmth and give the hair a natural look usually follows hair lightening. The disadvantages to following the lightening process with such a toning process include additional products needed for the service, additional time necessary to perform the service and the additional cost of the service.

The above-described category 2 bleach medium is intolerant of most dyes. The combination of the high alkalinity and stronger oxidizing conditions act synergistically to destroy most dye molecules within a short period of time.

The patent literature includes only a few references in relation to compositions that simultaneously lighten the hair by more than four levels and deposit coloring tone at the same time. The dyes that have been identified to date that are both stable in powder bleaches and capable at the same time of dyeing hair efficiently are limited. For example, U.S. Pat. No. 5,688,291 to Said includes in the bleach composition disperse dye molecules which are stable in the bleach and are capable of depositing desired tones on the hair. Note, however, disperse dyes are only slightly soluble in water and must be blended in the dry form in the bleach powder composition for use.

U.S. Pat. Nos. 2,991,228 and 5,224,964 disclose the use of pigment-type colorants blended into bleach powder. Although the colorants are stable in the bleaching medium, they are unable to deposit significant tone to the hair.

What is desired is a bleach and coloring composition that can lightened the hair up to seven levels and effectively deposit coloring.

SUMMARY OF THE INVENTION

The present invention provides a single step process and composition of a category 2 bleach system which can simultaneously lighten the hair up to seven levels and effectively neutralize undesirable warmth that accompanies the lightening process, provide natural tones or deposit fashion shades. This is achieved by including in the bleach mixture a solution containing basic dye molecules that have been found to be stable in the bleach and capable of depositing the desired amount of tone on the hair.

More particularly, the invention comprises a powder bleach composition including a basic dye, that remains active in the bleach and can impart toning or coloring to the lightened hair. The basic dyes found to be useful in the invention are typically azo dyes.

The advantages of a powder bleach with a built-in toner composition are significant. A single-step process will reduce the amount of time of the hair lightening process. It reduces prolonged contact between the skin with alkalinity, peroxide and oxidation dyes. It also allows for single-step natural and fashion shades to be created on the hair.

Therefore, it is an object of the present invention to provide a hair bleach composition that can lighten up to seven levels and includes dye for adding coloring to the lightened hair.

It is another object of the present invention to provide hair bleach and coloring composition including a basic azo dye that is stable in the bleach and can impart toning or coloring to hair.

It is a further object of the present invention to provide a powder bleach and basic dye composition that is stable and may be applied to hair in a single step for both bleaching the hair up to seven levels and effectively neutralizing the undesirable warmth that accompanies the lightening process.

It is yet another object of the present invention to provide a one-step method of applying a bleach and coloring composition that can simultaneously lighten hair up to seven levels while effectively adding coloring.

It is yet a further object of the present invention to provide a one-step method of applying a bleach and coloring composition including a basic azo dye that is stable in the bleach and can impart toning or coloring to hair.

It is still another object of the present invention to provide a one-step method of applying a powder bleach and coloring composition that is stable for both bleaching the hair up to seven levels and effectively neutralizing the undesirable warmth that accompanies the lightening process.

Still other objects and advantages of the invention will in part be obvious and will in part be apparent from the specification.

In accordance with the present invention, these and other objectives are achieved by a single-step process and composition of hair bleach, which can simultaneously lighten the hair up to seven levels and effectively neutralize any undesirable warmth, provide natural tones or deposit fashion shades. This is achieved by including in the powder bleach mixture a solution containing basic dye molecules, which in the present invention have been found to be both stable in the bleach and capable of depositing the desired amount of tone on the hair. The preferred dyes generally fall into the class of water-soluble basic azo compounds.

The invention accordingly comprises the several steps and the relation of one or more of such steps with respect to each of the others, and the composition embodying elements, all as exemplified in the following detailed disclosure.

DETAILED DESCRIPTION OF THE PREFERRED EMBODIMENTS

Hundreds of colorants were screened to achieve the present invention, namely to create a single-step bleach system which lightens the hair by more than four levels, and at the same time, neutralizes undertones or imparts a desired natural or fashion shade. The dyes tested generally belong to the class of basic dyes. The dyes were tested for four properties: 1) stability in a hair conditioner, 2.) stability in a category 2 bleach medium, 3.) the ability to color hair, and 4.) the color fastness or permanency of the deposited color on hair.

The testing procedure used to screen the dyes consisted of two steps: 1.) each dye to be tested was solubilized and incorporated into a typical hair conditioner base, and 2.) The hair conditioner/dye solution was combined with a typical category-2 bleach and a 6% hydrogen peroxide solution. Any commercial bleach powder and peroxide solution could have served the purpose to be used with the conditioner and the solubilized dye. For example, Basic White 2, a widely popular bleach powder and Clairoxide 20 Volume Developer may be used. Both are trademarks of Clairol, Inc. of Stamford, Conn. Or, for example, Wella Blondor Powder Lightener and Wella 20 Volume Crème Developer may be used. Both are trademarks of the Wella Corporation of Montvale, N.J.

For the testing, the concentration of the dye in the hair conditioner was 1.5% by weight. Twenty-five grams of dye/hair conditioner, twenty-five grams of bleach powder and twenty-five grams of a 6% hydrogen peroxide solution were mixed in a plastic bowl. Using a brush, this bleach and coloring composition was applied to two sets of natural white and medium brown hair swatches. The swatches were wrapped in aluminum foil. One set was incubated at 45° C. and one set processed at room temperature (25° C.). The remaining bleach and coloring composition in the bowl was monitored for color changes associated with instability.

If the oven-treated hair swatches revealed significant color deposit and if there was no appreciable color breakdown in the bowl or foil, then another set of swatches would be treated with the same bowl mixture, which had now been left to age for at least 30 minutes. This delay in using the bleach and coloring composition simulates the time required to complete a normal bleach application in the salon. The second set used should obtain substantially the same level of color deposit as the first set.

Once the dye was found to be acceptable in terms of color deposit and stability in the bleach powder, it would be assessed for color durability with repeated cycles of shampooing with a mild shampoo followed by drying. If the color intensity is visually maintained in the hair, the color is considered permanent.

The greatest majority of dyes tested failed at least one of the criteria. The typical oxidative dyes that are commonly used in haircolor products are not stable in a category 2 bleach medium and were not deemed effective under these criteria. Examples of oxidative dyes that were deemed unsuccessful include, p-phenylenediamine, p-aminophenol, 1-naphthol and resorcinol. Basic dyes with structure other than an azo structure also failed the testing procedure and criteria. Examples of other basic dyes that were deemed unsuccessful include, but are not limited to, the following: Basic Violet 4 (a derivative of triphenylmethane), Basic Blue 9 (a derivative of thiazine) and Basic Blue 3 (a derivative of oxazine).

The present invention relates to a small number of colorants, which are generally used widely in the textile and paper industries, which were identified as satisfying the testing criteria. The dyes belong generally to the basic class of dyes, and typically, basic azo-type dyes. Many of the dyes identified and used herein in the present invention, their molecular structures and their chemical properties, are proprietary information of the dye manufacturers. Nonetheless, the dyes are readily available in the market and may often be obtained from any of several manufacturers.

In general, basic dyes are readily soluble in water. The solubility of the dyes is important because the uptake of the dye molecules by hair fibers takes place from the aqueous phase. Dispersing agents or co-solvents, such as benzyl alcohol and the like, can further modify solubility.

Several of the basic dyes that the present invention found to be of value are listed in Table 1. Many dyes are also listed under its generic Colour Index (CI) name.

| Dye | Chemical Class | C.I.# | Toning ability/Stability |
|---|---|---|---|
| Basic Blue 41 | Azo | 11154 | 3 |
| Basic Blue 54 | Azo | 11052 | 1 |
| Basic Blue 67 | Azo | 45175 | 4 |
| Basic Brown 1 | Azo | 21000 | 2 |
| Basic Brown 4 | Azo | 21010 | 2 |
| Basic Brown 16 | Azo | | 1 |
| Basic Orange 1 | Azo | 11320 | 1 |
| Basic Orange 2 | Azo | 11270 | 1 |
| Basic Red 18 | Azo | 11085 | 5 |
| Basic Red 22 | Azo | 11055 | 4 |
| Basic Red 46 | Azo | | 5 |
| Basic Red 76 | Azo | 12245 | 0 |
| Basic Red 104 | Azo | | 5 |
| Basic Violet 35 | Azo | | 4 |
| Basic Yellow 45 | Azo | | 2 |
| Basic Yellow 57 | Azo | | 2 |
| Basic Yellow 67 | Azo | | 2 |

The dyes have been assigned arbitrary units on a scale of 0 to 5 to indicate their performance in the category 2 bleach medium. They have been rated for toning ability and stability in a bleach medium. Any color that was deposited on hair swatches was visually assessed and given a rating. A dye with a rating of (5) means outstanding toning features and stability, while a rating of (0) indicates both lack of toning and instability in a bleach medium. Generally, dyes rated 0 to 1 may be either too unstable in the bleach composition or otherwise ineffective in depositing tone.

Each of the basic dyes listed in Table 1 may be commercially available under one or more of the trade names listed in Table 2. The list is representative only and does not include all suppliers of Basic dyes. A more comprehensive list may be referenced in Textile Chemist and Colorist Buyers' Guide or the Colour Index, 3rd Edition, Volume 5, pages 5073–5086.

| Dye | Tradename | Manufacturer |
|---|---|---|
| Basic Red 22 | Akoyl Red B | Aakash Chemicals and Dyestuffs, Inc. |
| Basic Red 22 | Maxilon Red BLN (liq.) | Ciba Specialty Chemicals Corp. |
| Basic Red 46 | Basacryl Red XGRLS | D&G Dyes, Inc. |
| Basic Red 46 | Maxilon Red GRL | Ciba Specialty Chemicals Corp. |
| Basic Red 46 | Rico Basic Red GRL | Rite Industries, Inc. |
| Basic Blue 41 | Basacryl Blue GRL X3GLS | D&G Dyes, Inc. |
| Basic Blue 41 | Orcozine Blue GRLA 300% | Organic Dyestuffs Corp. |
| Basic Brown 1 | Bismark Brown Y | John Campbell & Co., Inc. |
| Basic Brown 4 | Lowacryl Brown 4 | J. H. Lowenstein & Sons, Inc. |
| Basic Brown 4 | Bismark Brown R | Passaic Color and Chemical Co. |

Some basic dyes have been used as color enhancing agents. For example, there are many commercially available shampoos and conditioners that are designed to deposit tone on hair. The wearability of the color deposit is only temporary and is quickly washed out of the hair. The wearability of the color from shampoos and conditioners can be slightly improved with heat application and cosolvents well know by those of ordinary skill in the art. However, this type of product will only deposit tone on the natural hair, and is not capable of simultaneously lightening the base color of the hair. This does not allow for results that are lighter than the starting base. Basic dyes have never, prior to this invention, been used in a category 2 bleach medium.

In what follows, specific examples will be cited to illustrate the applicability of the present invention. Of course, it will be recognized by those of ordinary skill, that the following examples are illustrative and in no way limit the scope of the invention. The present invention covers a bleach and coloring composition and a method of using the composition to lighten hair up to seven levels and simultaneously deposit tones to effectively neutralize any undesirable warmth, provide natural tones or deposit fashion shades. The system consists of three separate components, specifically, a bleach powder, a hydrogen peroxide solution or other source of oxygen and a solution of soluble basic dyes, and preferably azo dyes. In a preferred embodiment, the three components are used together in a single step.

The bleach powders useful in the invention are well-known in the art. For example, Clairol, Inc makes a bleach powder called Basic White 2 containing the ingredients: ammonium persulfate, disodium EDTA, hydrated silica; hydroxypropyl methylcellulose, potassium persulfate, sodium metasilicate, which sets the standard for bleach powders in the industry. Redken Laboratories, Inc. make the bleach powder called Lift 5/15. This product contains potassium persulfate, kaolin, sodium metasilicate, sodium persulfate, hydrated silica, guar gum, and EDTA. Lift 5/15 is a gentle no-ammonia formula. Of course, any bleach powder capable of more than 4 levels of lift when combined with an activator, such as a hydrogen peroxide solution, can be used in the invention.

The preferred basic azo dyes useful in the invention can be selected from those described above. Additional soluble basic dyes in accordance with the generic description below (Formula 1) may also be used.

The following example illustrates the testing composition used to determine the efficacy of a given dye in the invention. Component 1 is a typical bleach powder used to lighten the color of the hair four or more levels. It will be well recognized in the art that numerous variations are possible in a bleach powder, including amounts of active ingredients and types of fillers, surfactants, thickeners, or other additives.

| Component 1 - Bleach Powder | |
|---|---|
| Potassium Persulfate (active ingredient) | 36.5% |
| Sodium Persulfate (active ingredient) | 19.0% |
| Ammonium Persulfate (active ingredient) | 7.5% |
| Hydroxypropyl Methylcellulose (thickener) | 3.0% |
| Silica (additive) | 0.5% |
| Disodium EDTA (surfactant) | 0.5% |
| Sodium Silicate (filler) | 33.0% |

Component 2 presents a developer or hydrogen peroxide solution used to activate and provide oxygen for lightening the hair. Developers may be as simple as hydrogen peroxide, water and stabilizer, or may contain thickeners such as cetyl alcohol and the like, surfactants such as nonoxynol-9 and the like, or other additives such as emulsifiers and polymeric thickeners and the like. The concentration of hydrogen peroxide determines the amount and speed of the lightening process. The typical percentage range of hydrogen peroxide commercially used is between about 2% to about 12%.

| Component 2 - Hydrogen Peroxide Developer | |
|---|---|
| Water | 87.8% |
| Hydrogen Peroxide (50%) | 12.0% |
| Phosphoric Acid | 0.2% |

Component 3 is a suitable vehicle for the dyes. As a matter of illustration, a typical hair conditioner base may be used to carry the dyes in solution. Other bases could be used with ingredients that are compatible with the cationic dyes of the invention. Because of the large number of potential dye combinations, only a few examples can be cited for the dye compositions. For example, Example 1 presents a dye combination used to neutralize undertones resulting when light brown or dark blonde is lightened. Example 2 provides an illustration of how dark brown hair can be transformed into auburn hair. The formula given in Example 3 demonstrates the capability of transforming dark brown or black hair to a vibrant pink fashion shade. The dye is added in about 1.5% to about 1.7% by weight for the test. However, the dye may be used in amounts as low as 0.009% and as much as 2.2%, depending on the amount of coloring to be obtained.

EXAMPLE 1

Toning of Light Brown Hair

| Water | 84.80% |
|---|---|
| Cetearyl Alcohol (viscosity builder) | 5.25% |
| Behentrimonium Methosulfate (conditioner) | 1.75% |
| Oleyl Alcohol (viscosity builder) | 1.00% |
| Steareth-21 (emulsifier) | 2.50% |
| Benzyl Alcohol (co-solvent) | 2.00% |
| Basic Brown 1 | 0.822% |
| Basic Yellow 45 | 0.293% |
| Basic Blue 67 | 0.585% |
| Propylene Glycol (humectant) | 0.56% |
| Diazolidinyl Urea (preservative) | 0.30% |
| Methylparaben (preservative) | 0.11% |
| Propylparaben (preservative) | 0.03% |

EXAMPLE 2

Converting Dark Brown Hair to Auburn

| Water | 84.80% |
|---|---|
| Cetearyl Alcohol (viscosity builder) | 5.25% |
| Behentrimonium Methosulfate (conditioner) | 1.75% |
| Oleyl Alcohol (viscosity builder) | 1.00% |
| Steareth-21 (emulsifier) | 2.50% |
| Benzyl Alcohol (co-solvent) | 2.00% |
| Basic Yellow 45 | 1.400% |
| Basic Red 46 | 0.085% |
| Propylene Glycol (humectant) | 0.56% |
| Diazolidinyl Urea (preservative) | 0.30% |
| Methylparaben (preservative) | 0.11% |
| Propylparaben (preservative) | 0.03% |

EXAMPLE 3

Converting Black Hair to Fashion Pink

| Water | 84.80% |
|---|---|
| Cetearyl Alcohol (viscosity builder) | 5.25% |
| Behentrimonium Methosulfate (conditioner) | 1.75% |
| Oleyl Alcohol (viscosity builder) | 1.00% |
| Steareth-21 (emulsifier) | 2.50% |
| Benzyl Alcohol (co-solvent) | 2.00% |
| Basic Red 46 | 0.800% |
| Basic Violet 35 | 0.900% |
| Propylene Glycol (humectant) | 0.56% |
| Diazolidinyl Urea (preservative) | 0.30% |
| Methylparaben (preservative) | 0.11% |
| Propylparaben (preservative) | 0.03% |

Each of the above examples has been shown to provide effective coloring of bleach-lightened hair from application of the single bleached and coloring composition described.

Therefore, a class of dyes has been shown to be oxidatively stable and effective in coloring hair when contained in a bleach powder solution. The dyes belong generally to the class of soluble, azo basic dyes. The dyes of this class owe their name to fact that the dyes ionize with the colored component constituting the cation. There are many dyes that belong to this class and they vary considerably in their structure. Structures identified as basic dyes include derivatives of triphenylmethane, diphenylmethane, thiazine, oxazine, acridine, azines, xanthenes, anthraquinones and azo groups. Hundreds of colorants were screened to achieve the present invention. The dyes identified as acceptable for the present invention consist generally of basic dyes with an azo structure.

In general, the dyes used herein are basic azo dyes including an anion counter-ion. When such dyes ionize, the colored component constitutes the cation. As is well known, azo dyes may be synthesized by the diazotization of aromatic amines, followed by coupling to further aromatic compounds (known as coupling components). The result is the azo group, —N═N—. The basic azo dyes will typically have the following generic base formula, as shown in Formula 1.

Formula 1: Basic Azo Dyes

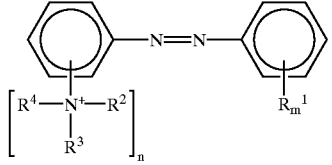

wherein
R$^1$ is selected from the group consisting of:
  R$^5$; N(R$^5$)$_2$; N$^+$(R$^5$)$_3$; CN and X;
and wherein each of R$^2$, R$^3$, R$^4$ and R$^5$ are independently selected from the group consisting of:
  C$_{1-4}$ alkyl;
  C$_{1-8}$ substituted alkyl, wherein the substituents are selected from the group consisting of CN, (OR$^6$)$_y$, O(O)CR$^6$$_y$, and X, wherein R$^6$ is selected from the group consisting of H and C$_{1-4}$ alkyl, and y is an integer from 1 to 3 inclusive;
  H; and
  O;

and wherein X is a halogen; m is an integer from 1 to 4 inclusive; and n is an integer from 1 to 3 inclusive.

Specific dyes within this family will have substituents at various positions, as shown in Formula 2, Formula 3 and Formula 4.

Formula 2: Basic Red 22

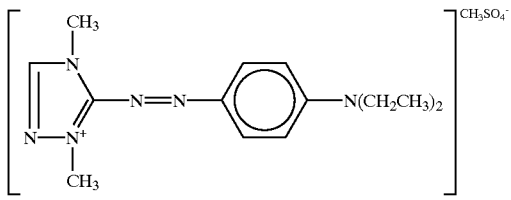

Formula 3: Basic Red 46

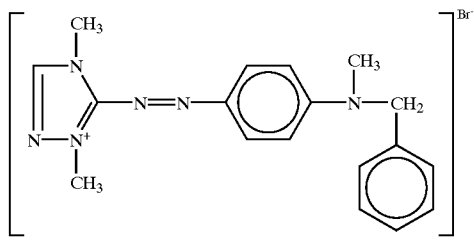

Formula 4: Basic Yellow 57

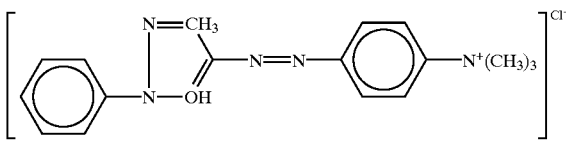

A method of using the bleach and coloring composition of the invention will now be described. As is well-known in the art, category 2 bleaches are generally applied by professional hair care technicians in a salon or beauty parlor. The customer's hair may be washed and dried first. The technician mixes the powder bleach component, the activator and the dye medium in a plastic bowl to form a thick liquid. The liquid is applied to the hair by the technician and allowed to set for up to 20 minutes or more, depending on the level of lift to be obtained. Then, the solution is rinsed off, and often a conditioner applied.

Note, as is well understood by those practicing this art, the mixture of the category 2 bleaching composition, the dyeing composition and the oxidizing composition can include each component in a concentration ranging from about 15% to about 40% by weight relative to the total weight of the mixture. Preferably, the components are present in approximately equivalent amounts.

The processing times of hair lighteners are dependent on the amount of lightening desired. The times generally range from 1 minute (very little lightening) to about 60 minutes (maximum lightening). The timing is watched closely in the salon by the technician to achieve the desired results, and in fact, may include periodic visual assessment (i.e., strand test for a visual assessment). Typically, the time will be from about 10 minutes to about 45 minutes.

It will thus be seen that the objects set forth above, among those made apparent from the preceding description, are efficiently attained and, since certain changes may be made in carrying out the above methods and in the devices as set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope or the invention which, as a matter of language, might be said to fall there-between.

What is claimed is:

1. A method of simultaneously lightening and coloring hair comprising the steps of: mixing a category 2 bleaching composition in an amount sufficient to lighten the color of hair by more than four levels, a dyeing composition including at least one basic azo dye that is stable in said category 2 bleaching composition in an amount sufficient to color hair and an oxidizing composition; and applying said mixture to hair.

2. The method of claim 1 wherein said category bleaching composition includes a persulfate salt.

3. The method of claim 1 wherein said at least one basic azo dye is selected from the group consisting of: Basic Blue 41 (C.I. #11154), Basic Blue 67 (C.I. #45175), Basic Brown 1 (C.I. #21000), Basic Brown 4 (C.I. #21010), Basic Red 18 (C.I. #11085), Basic Red 22 (C.I. #11055), Basic Red 46, Basic Red 104, Basic Violet 35, Basic Yellow 45, Basic Yellow 57 (C.I. #12719) and Basic Yellow 67.

4. The method of claim 1 wherein said dyeing composition includes at least one oxidizing agent.

5. The method of claim 1 wherein said oxidizing composition is present in a composition separate from said dyeing composition.

6. The method of claim 1 wherein said dyeing composition includes a mixture of basic azo dyes selected from the group consisting of: Basic Blue 41 (C.I. #11154), Basic Blue 67 (C.T. #45175), Basic Brown I (C.I. #21000), Basic Brown 4 (C.I. #21010), Basic Red 18 (C.I. #11085), Basic Red 22 (C.I. #11055), Basic Red 46, Basic Red 104, Basic Violet 35, Basic Yellow 45, Basic Yellow 57 (C.I. #12719) and Basic Yellow 67.

7. The method of claim 1 wherein said at least one basic azo dye is present in a concentration ranging from about 0.009% to about 2.2% by weight relative to the total weight of said dyeing composition before it is mixed with said oxidizing composition.

8. The method of claim 1 wherein said at least one basic azo dye is present in a concentration ranging from about 1.5% to about 1.7% by weight relative to the total weight of said dyeing composition before it is mixed with said oxidizing composition.

9. The method of claim 1 wherein said oxidizing composition includes aqueous hydrogen peroxide.

10. The method of claim 9 wherein said oxidizing composition includes hydrogen peroxide in a concentration ranging from about 2% to about 12% by weight relative to the total weight of said oxidizing composition.

11. The method of claim 1 wherein said category 2 bleaching composition is a powder of persulfate salts of at least one of ammonium, potassium and sodium, and salts of at least one of silicate and carbonate.

12. The method of claim 1 wherein the mixture of said category 2 bleaching composition, said dyeing composition and said oxidizing composition has a pH of from about 9 to about 11.

13. The method of claim 1, further comprising the steps of: allowing the mixture of said category 2 bleaching composition, said dyeing composition and said oxidizing composition to remain on said hair for a time sufficient to lighten and color said hair; and subsequently rinsing said hair.

14. The method of claim 13 wherein said time is from about 1 minute to about 60 minutes.

15. The method of claim 14 wherein said time is from about 10 minutes to about 45 minutes.

16. The method of claim 1 wherein the mixture of said category 2 bleaching composition, said dyeing composition and said oxidizing composition has each of said category 2 bleaching composition, said dyeing composition and said oxidizing composition present in a concentration ranging from about 15% to about 40% by weight relative to the total weight of said mixture.

17. The method of claim 16 wherein each of said category 2 bleaching composition, said dyeing composition and said oxidizing composition is present in approximately equivalent amounts.

18. The method of claim 1 wherein said hair is human hair.

19. The method of claim 18 wherein the mixture of said category 2 bleaching composition, said dyeing composition and said oxidizing composition bleaches said human hair and neutralizes the accompanying warmth.

20. A composition useful for simultaneously lightening and coloring hair, comprising: a category 2 bleach including a persulfate salt in an amount sufficient to lighten the color of hair by more than four levels; at least one basic azo dye selected from the group consisting of: Basic Blue 41 (C.I. #11154), Basic Blue 67 (C.I. #45175), Basic Brown 1 (C.I. #21000), Basic Brown 4 (C.I. #21010), Basic Red 18 (C.I. #11085), Basic Red 22 (C.I. #11055), Basic Red 46, Basic Red 104, Basic Violet 35, Basic Yellow 45, Basic Yellow 57 (C.I. #12719) and Basic Yellow 67, in an amount sufficient to color hair; and an oxidizer including aqueous hydrogen peroxide.

* * * * *